United States Patent [19]

Teetz et al.

[11] 4,361,482
[45] Nov. 30, 1982

[54] CHROMATOGRAPH FOR PRESSURE CHROMATOGRAPHY

[75] Inventors: Volker Teetz, Hofheim am Taunus; Rainer Uhmann, Kriftel; Rudolf Knapp, Eppstein, all of Fed. Rep. of Germany

[73] Assignee: Hoechst Aktiengesellschaft, Frankfurt am Main, Fed. Rep. of Germany

[21] Appl. No.: 309,455

[22] Filed: Oct. 7, 1981

[30] Foreign Application Priority Data

Oct. 9, 1980 [DE] Fed. Rep. of Germany ....... 3038132

[51] Int. Cl.³ .............................................. B01D 15/08
[52] U.S. Cl. .................................... 210/198.2; 55/386
[58] Field of Search ........................ 210/198.2; 55/386

[56] References Cited

U.S. PATENT DOCUMENTS 3,487,938  1/1970  Patterson .......................... 210/198.2
3,966,609  6/1976  Godbille ............................ 210/198.2

Primary Examiner—John Adee
Attorney, Agent, or Firm—Curtis, Morris & Safford

[57] ABSTRACT

In this chromatograph for pressure chromatography, a plunger having a plunger stem is arranged so that it can move within the separation column (3). On the front face of the plunger there is a collecting space (7) for liquid, which is covered by a frit (6) and which has a connecting line (8) to the face of the plunger opposed to the front face. In order to prevent abrasive and chemical attack by the column packing on the plunger, its seal and the cylinder wall of the separation column, the plunger should comprise a lower part (2) having a device (4) to accommodate the plunger stem (5), and an upper part (1), the two parts being arranged so that they can move in relation to one another. The upper part (1) has a centering peg (9) which projects into the lower part (2). A spring (12) on which the upper part (1) is supported, is located concentrically in relation to the peg (9). The upper part (1) has recesses on its circumference to accommodate at least two seals (19 and 21) and a ring channel (16) which is formed by a retaining ring (13) for one seal (19) and is connected to the collecting space (7). The other seal (21) is held in its recess by a ring (23) which is located concentrically around the spring and is supported by the lower part.

2 Claims, 1 Drawing Figure

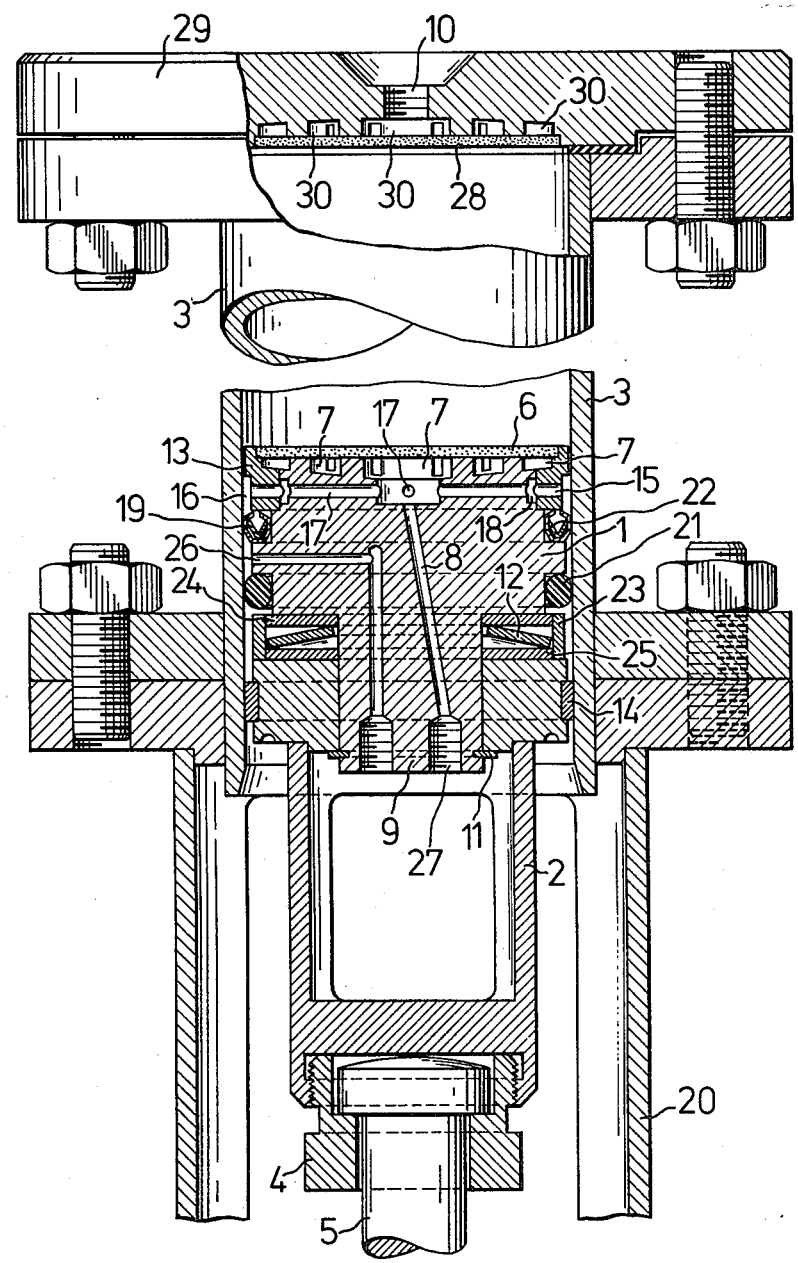

CHROMATOGRAPH FOR PRESSURE CHROMATOGRAPHY

The invention relates to a chromatograph for pressure chromatography, comprising a separation column having a plunger arranged so that it can move within the column.

A separation column for chromatographic purposes which has within it a pneumatic plunger fitted with a simple sealing ring is known from G-I-T Fachzeitschrift für Laboratorium, 20th year of publication, 1976, page 821. After the separation column has been filled with a suspension composed of a stationary phase, for example silica gel and migrating agent, the stationary phase is axially compressed and consolidated by loading the plunger.

A column packing which remains largely homogeneous during the separation process, is obtained. A disadvantageous factor in this chromatograph is the design of the plunger, since it is not possible to prevent abrasive and chemical attack by the column packing on the plunger, in particular its seal, and the cylinder wall of the separation column.

The intention of the invention is to provide a remedy for this. The invention, as characterized in the claims, solves the problem by means of a plunger comprising a lower part having a device to accommodate the plunger stem, and an upper part, the two parts being arranged so that they can move in relation to one another, the upper part having a centering peg which projects into the lower part, a spring on which the upper part is supported being located concentrically in relation to the peg, the upper part having recesses on it circumference to take at least two seals and a ring channel which is formed by a retaining ring for one seal and is connected to the collecting space, the other seal being held in its recess by a ring which is located concentrically around the spring and is supported by the lower part.

It can be advantageous to fit a leakage line between the seals.

The advantages achieved by means of the invention can be seen essentially in the fact that the abrasive attack on the plunger and seals is prevented to a large extent, and it becomes possible to provide, during the separation, a satisfactory and permanent seal between the cylinder wall and the plunger, which seal is required for the separation process to take place in a trouble-free manner.

In the following text, the invention is illustrated in greater detail by means of a drawing which shows only one embodiment.

The separation column 3, preferably made of high-quality steel, is closed at one end by a movable plunger comprising a lower part 2 and an upper part 1, which can be moved in relation to one another. The lower part 2 is equipped with a device 4 to accommodate the plunger stem 5. The upper part 1, which has on its front face a collecting space 7 for the liquid, which is covered by a sintered plate 6 and which has a connecting line 8 to the face of the plunger opposite the front face, has a peg 9. This peg 9 projects into the lower part 2. It centers the two parts of the plunger. On its end there is a groove to accommodate a securing ring 11. A spring 12, for example a Belleville spring (disk spring) which rests on the lower part 2 and on which the upper part 1 is supported, is arranged concentrically in relation to the peg 9. The upper part has a retaining ring 13 and the lower part has a plunger ring 14. The retaining ring 13 supports the sintered plate 6, which covers the collecting space 7, and forms the ring channel 16, which is connected to the collecting space 7 via at least one drilled hole 15, the ring channel 18 and the drilled hole 17. The retaining ring 13 at the same time secures the seal 19 which is located in a recess. While the packing of the separation column is compressed, liquid flows from the collecting space 7 into the ring channel 16 and thus prevents the stationary phase from penetrating into the gap between the plunger and the cylinder wall, and prevents, in particular, this phase from reaching the seal 19. A seal having a U-shaped cross-section with a radially acting spring 22 located in the cavity, has proved suitable as the seal 19. The seal 21 is located in the recess. It is kept in position by means of a ring 23 which is supported by the lower part 2 and is centered, if necessary, by disks 24 and 25. A leakage line 26 can, if necessary, be fitted between the seals 19 and 21. Moving the upper part 1 and the lower part 2 towards one another causes the seal 21 to be deformed by the ring 23 and thus pressed onto the cylinder wall. The spring constant of the spring 12 is appropriately such that the parts of the plunger are kept apart during the compression process, that is to say only the seal 19 becomes effective. Only after the stationary phase has been compressed should the lower part 2 move towards the upper part 1 and the ring 23 press onto the seal 21, so that, in the stationary state of the plunger, the seal 21 also becomes effective in addition to the seal 19. A strong current of liquid if forced through the plunger during the compression via the connecting element 27.

The other end of the separation column is closed by a frit 28 and the flange-like lid 29. Within the lid 29 there is also a collecting space 30 for the liquid and, associated therewith, a means 10 of connecting a line.

20 indicates the mounting for the chromatograph.

We claim:

1. A chromatograph for pressure chromatography, comprising a separation column which has, arranged so that it can move therein, a plunger which has a plunger stem and has, on its front face, a collecting space for liquid, which is covered by a frit and which has a connecting line to the face of the plunger opposite to the front face, wherein the plunger comprises a lower part having a device to accommodate the plunger stem, and an upper part, the two parts being arranged so that they can be moved in relation to one another, the upper part has a centering peg which projects into the lower part, a spring on which the upper part is supported, is located concentrically to the peg, the upper part has recesses on its circumference to accomodate at least two seals and a ring channel which is formed by a retaining ring for one seal and is connected to the collecting space, and the other seal is held in its recess by a ring which is located concentrically around the spring and is supported by the lower part.

2. A chromatograph as claimed in claim 1, wherein a leakage line is fitted between the seals.

* * * * *